United States Patent [19]
Keilbach et al.

[11] Patent Number: 5,931,161
[45] Date of Patent: Aug. 3, 1999

[54] ON-AIRWAY RESPIRATORY GAS MONITOR EMPLOYING TRANSFORMED INFRARED SIGNALS

[75] Inventors: Kevin A. Keilbach; D. Alan Hanna, both of Boulder, Colo.

[73] Assignee: Datex-Ohmeda, Inc., Louisville, Colo.

[21] Appl. No.: 09/040,558

[22] Filed: Mar. 18, 1998

[51] Int. Cl.⁶ .................................................. A61M 16/00
[52] U.S. Cl. ................................ 128/204.22; 128/204.23
[58] Field of Search ........................ 128/204.22, 204.21, 128/204.23, 204.28, 205.23, 205.24; 73/23.2, 23.3; 600/595, 409, 587, 546

[56] References Cited

U.S. PATENT DOCUMENTS

| | | | |
|---|---|---|---|
| 3,906,241 | 9/1975 | Thompson | 250/574 |
| 4,180,734 | 12/1979 | Gedeon | 250/345 |
| 4,552,164 | 11/1985 | Urella | 137/2 |
| 4,697,593 | 10/1987 | Evans et al. | 128/634 |
| 4,914,720 | 4/1990 | Knodle et al. | 250/343 |
| 4,928,703 | 5/1990 | Wong | 128/719 |
| 4,955,946 | 9/1990 | Mount et al. | 128/719 |
| 5,005,573 | 4/1991 | Buchanan | 128/207 |
| 5,046,018 | 9/1991 | Flewelling et al. | 364/497 |
| 5,081,998 | 1/1992 | Yelderman et al. | 128/719 |
| 5,092,342 | 3/1992 | Hattendorff et al. | 128/719 |
| 5,095,913 | 3/1992 | Yelderman et al. | 128/719 |
| 5,127,405 | 7/1992 | Alcala et al. | 128/633 |
| 5,130,544 | 7/1992 | Nilsson | 250/343 |
| 5,193,544 | 3/1993 | Jaffe | 128/634 |
| 5,213,109 | 5/1993 | Susi | 128/719 |
| 5,233,194 | 8/1993 | Mauze et al. | 250/341 |
| 5,261,415 | 11/1993 | Dussault | 128/719 |
| 5,282,473 | 2/1994 | Braig et al. | 128/664 |
| 5,296,706 | 3/1994 | Braig et al. | 250/339 |
| 5,326,973 | 7/1994 | Eckerbom et al. | 250/343 |
| 5,423,313 | 6/1995 | Olsson et al. | 128/204.21 |
| 5,649,531 | 7/1997 | Heinonen | 128/203.12 |
| 5,873,361 | 1/1999 | Hakala | 128/204.23 |

FOREIGN PATENT DOCUMENTS 0 309 666  4/1989  European Pat. Off. .

OTHER PUBLICATIONS

Amorphous Materials, Inc., Chalcogenide Glass Infrared Fibers For Application in the 2–11μm Wavelength Range.

Primary Examiner—John G. Weiss
Assistant Examiner—Charles W. Anderson
Attorney, Agent, or Firm—Holme Roberts & Owen LLP

[57] ABSTRACT

The respiratory gas analyzer (10), in one embodiment, is used for in-stream analysis of a patient breathing circuit (12). The analyzer includes a source (12) of infrared illumination, a modulator (28) for modulating the infrared illumination on a wavelength dependent basis to yield a modulated signal, a transmitter/detector unit (32) for transmitting the modulated signal through the breathing circuit (12) and detecting the transmitted signal, and a processing unit (34) for determining composition information regarding a sample under analysis based on the detected, modulated signal. The modulator (28) may include, for example, a Michelson interferometer for transforming the illumination into a frequency domain signal. The modulated signal allows for use of a compact detector system at the respiratory circuit interface. In addition, infrared fiber optics can be utilized to minimize instrumentation/optics at the interface.

25 Claims, 6 Drawing Sheets

ON-AIRWAY RESPIRATORY GAS MONITOR EMPLOYING TRANSFORMED INFRARED SIGNALS

FIELD ON THE INVENTION

The present invention relates in general to respiratory gas analyzers and, in particular, to a respiratory gas analyzer that utilizes transformed infrared signals to allow for multiple component gas analysis with a simplified detector system. The invention is particularly useful for on-airway applications where it is desirable to minimize instrumentation proximate to the patient.

BACKGROUND OF THE INVENTION

There are many commercial applications in which it is desirable to monitor the concentrations of components in gas streams. In particular, it is important for medical personnel to monitor the concentrations of the various components in a patient's respiratory stream to dispense the proper amount of medication and/or identify potentially hazardous conditions. This is especially important in the field of anesthesiology, where gaseous anesthetic or therapeutic agents, such as nitrous oxide, halothane, enflurane, desflurane, sevoflurane, and isoflurane, are dispensed to the patient in controlled dosages. Therefore, monitoring anesthesia may involve analyzing the respiratory stream with respect to one or more components, possibly including anesthetic or therapeutic agents, as well as other respiratory gases, such as carbon dioxide.

One type of instrument that has been employed for monitoring respiratory gases is the spectral gas analyzer. Spectral gas analyzers provide an indication of the presence and concentration of selected components in a gas sample based on the detected spectral composition of illumination transmitted through the gas sample. The gaseous components of interest can be characterized with regard to specific illumination absorption properties. For example, a particular gaseous component may be characterized by an absorption band at a particular wavelength or over a wavelength range. By comparing the intensity of transmitted and received illumination of a selected wavelength or range of wavelengths for a particular gas sample, information regarding the absorption characteristics and composition of the sample can be obtained.

In order to monitor a variety of respiratory gases as well as anesthetic agents and/or therapeutic agents, spectral gas analyzers typically employ infrared illumination. In particular, the components of interest generally have distinctive absorption spectra in the near to mid infrared spectral range. Accordingly, multiple component gas analyzers typically employ either multiple infrared sources or a single broad band infrared source. The resulting polychromatic signals are transmitted through a gas sample and detected by a detector system that is designed to analyze the signals with respect to multiple wavelengths. In this regard, multiple detectors or a single detector array associated with a variable wavelength filter may be employed. In either case, standard chemometric calculations based on the output of the detector system can be used to identify and quantify the gases of the sample so that this information can be reported to the instrument user.

For a number of reasons, multiple component infrared gas analyzers have generally been implemented with a side-stream system architecture. That is, a portion of the respiratory stream is diverted from the patient's respiratory circuit for analysis. First, infrared sources typically generate significant heat. For example, certain broad band sources are operated at a temperature in excess of 900° C. in order to provide the desired illumination intensity across the infrared range of interest. It is, of course, desirable to locate such a heat source at a suitable distance from the patient. Moreover, in order to reduce optical losses and alignment concerns associated with mirrors and other conventional infrared optical elements, it is desirable to minimize the optical path length, and simplify the path configuration, between the source and the sample to be analyzed. Accordingly, various optical considerations have been thought to favor side-stream architectures. Moreover, the detector systems employed for multiple component infrared gas analysis tend to be massive and bulky. Because space in proximity to the patient is generally at a premium during medical procedures, it has been thought advantageous to locate the detector systems and associated processing equipment remote from the patient. Thus, both optical and space-related considerations have led to the acceptance of side-stream architectures for multiple component infrared gas analysis in the medical environment.

SUMMARY OF THE INVENTION

It has been recognized that the side-stream architecture has certain design limitations for multiple component infrared analysis. First, the gas sample in side-stream analyzers generally travels a significant distance from the patient to a sample chamber thereby limiting system response and accuracy. The side-stream architecture also increases system complexity and pneumatics hardware. Moreover, the side-stream diverted from the patient's respiratory circuit must be handled carefully. In this regard, it will be appreciated that the side-stream may contain potentially harmful or even carcinogenic materials including, for example, oxides of nitrogen and radioactively tagged particles depending in part of the nature of the medical procedure involved. It would therefore represent a significant advancement in respiratory gas analysis if the significant advantages of multiple component infrared gas analysis could be achieved in connection with an on-airway system architecture for allowing direct analysis of the respiratory stream in proximity to the patient.

The present invention is directed to a method and apparatus for multi-component, infrared gas analysis that is suitable for in-stream applications. The invention thereby allows for multiple-component infrared analysis of a respiratory stream proximate to the patient for improved response and accuracy. Moreover, side stream pneumatics and certain optical hardware can be eliminated thus simplifying system design. Eliminating the side stream gas flow also reduces handling of potentially harmful gases, further simplifying design. In this regard, the patient respiratory stream can remain entirely within the patent respiratory circuit for handling by existing respiratory circuit components, e.g., scrubbers, filters, vents and the like. Moreover, these advantages can be achieved in accordance with the present invention without unduly cluttering potential working areas near the patient.

According to one aspect of the present invention, fiber optics are used to transmit infrared illumination from a remote source to an analysis location in the patient respiratory circuit near the patient. The source provides illumination having a spectral composition sufficient for multiple component analysis. In this regard, the source preferably produces illumination extending across a continuum of wavelengths between about 4–8 microns and, more preferably across the wavelength range of about 2–12 microns. A fiber optical light guide forms a portion of an optical pathway between the source and the analysis location. The light guide is formed from fiber optics adapted for transmitting illumination in the wavelength range needed for infrared analysis. The illumination transmitted through the respiratory stream is received by a detector. The detector can be located at the analysis location, or it can be remotely located and optically interconnected to the analysis location via a further light guide. Preferably, the detector is of compact constructions and can be located at the analysis location so as to further reduce optical components and simplify system design. The detector is further associated with a processor for determining composition information regarding the respiratory sample under analysis based on an output from the detector.

According to another aspect of the present invention, illumination from a source is modulated on a wavelength dependent basis to yield a modulated signal for respiratory gas analysis. The source provides illumination having a number of wavelengths, e.g., a continuum of infrared wavelengths extending at least across the 4–8 micron range. The illumination is received by a modulator that transforms the illumination into a modulated signal wherein a first wavelength of the illumination is modulated at a first frequency and a second wavelength of the illumination is modulated at a second frequency different than the first frequency. In one embodiment, the modulator includes a Michelson interferometer operative for providing a modulated signal that is the Fourier transform of the illumination transmitted by the source.

The transformed signal is transmitted through a respiratory gas sample and received by a detector system. A second reference signal useful for processing purposes may be transmitted to the detector system via a reference path that does not pass through the sample gas. The detector system may include a single detector for detecting the modulated signal or multiple detectors positioned at selected locations to receive illumination transmitted through the gas sample on different paths having different path lengths. Such a multiple detector structure may be employed, for example, to allow the analyzer to monitor multiple components of the sample having different absorption sensitivities with similar measurement accuracies. The output from detector system is then deconvolved to yield wavelength related information and standard chemometric calculations can be used to identify and quantify components of the sample gas. It will be appreciated that such an analyzer system is particularly useful for in-stream applications because a simple, compact and lightweight detector system, for example, including only a single or small number of detectors, can be employed for detecting the modulated signal. Such a design also has a number of optical efficiency advantages as will be described below.

According to a further aspect of the present invention, a transmitter/detector unit is provided for engaging a patient's respiratory circuit to perform respiratory gas analysis in-stream adjacent to the patient. The unit includes: mounting structure, such as a molded plastic mount, for engaging a portion of the respiratory circuit; optics support structure for supporting fiber optics for transmitting an infrared, Fourier modulated optical signal through the engaged portion of the respiratory circuit; and detector support structure for supporting a detector system for detecting the infrared, Fourier modulated signal transmitted through the respiratory circuit and providing an output signal based on the detected, modulated signal, wherein the fiber optics and detector are supported in optical alignment with the engaged portion of the respiratory circuit disposed therebetween. The engaged portion of the respiratory circuit may be a separate conduit of the respiratory circuit, or may be formed by an integral, internal passageway of the unit. In the latter case, the unit can simply be interposed within the patient respiratory circuit using standard plastic breathing conduit connectors. The unit may further include structure for supporting reference path fiber optics wherein a reference signal is transmitted to the detector system via a reference path that does not traverse the respiratory circuit. The unit thereby allows for in-stream, infrared analysis of the respiratory circuit using a Fourier modulated signal with attendant advantages as set forth below.

DESCRIPTION OF THE DRAWINGS

For a more complete understanding of the present invention and further advantages thereof, reference is now made to the following detailed description, taken in conjunction with the drawings, in which.

DETAILED DESCRIPTION

Figure 1:
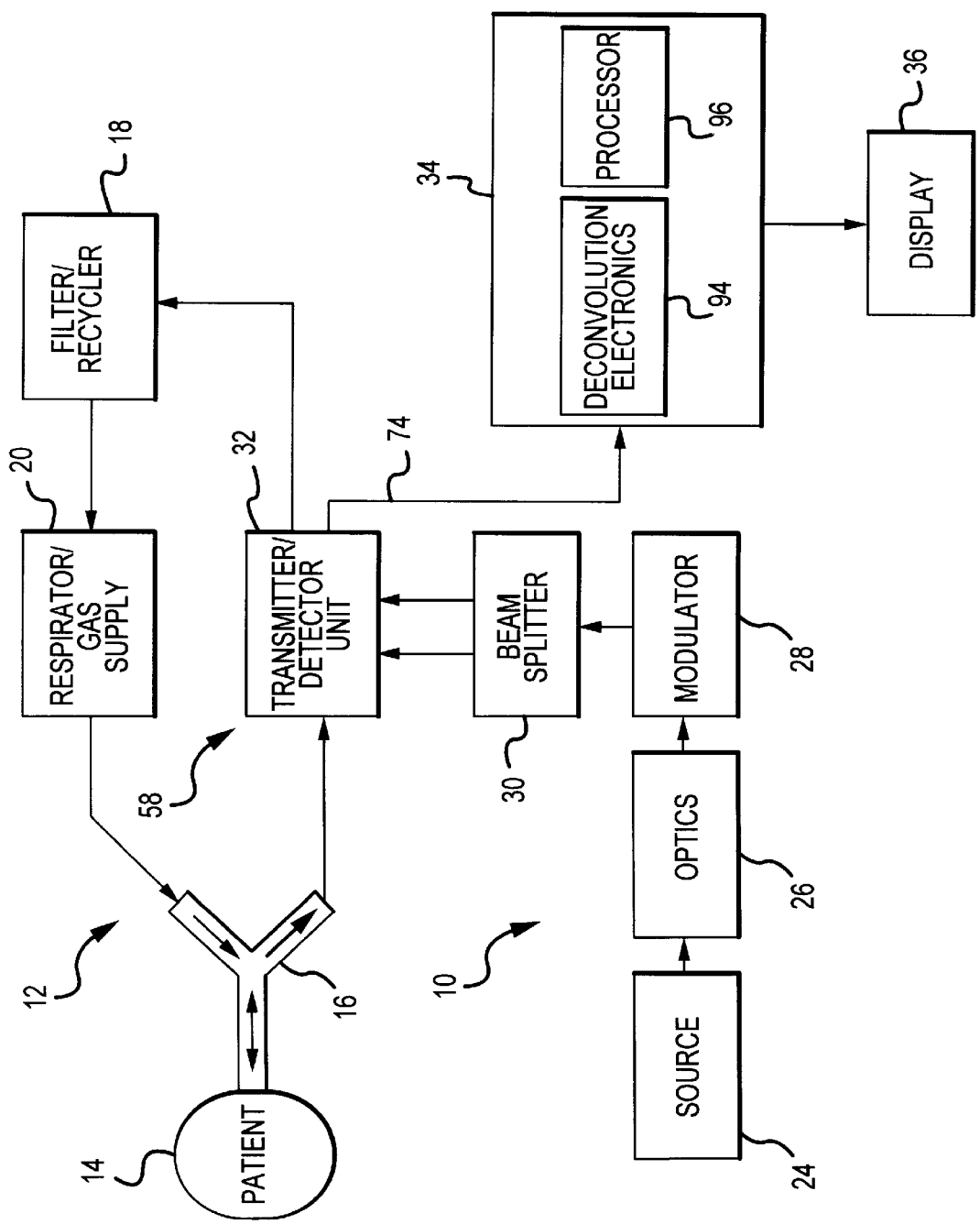
FIG. 1 is a schematic diagram showing an analyzer constructed in accordance with the present invention interfaced with a patient respiratory circuit.

In the following description, the invention is set forth in the context of an analyzer for performing in-stream analysis of a respiratory gas stream. It will be appreciated that various aspects of the invention are applicable to a side stream respiratory gas analysis application or other applications. Referring to FIG. 1, a respiratory gas analyzer in accordance with the present invention is generally indicated by the reference numeral 10. The analyzer 10 is used to monitor a patient respiratory circuit 12 for supplying respiratory and anesthetic or therapeutic gases to a patient 14 during a medical procedure. It will be appreciated that the nature of the gases delivered to the patient 14 may be varied depending on the medical procedure involved. In this regard, the gas stream delivered to the patient 14 may include anesthetic agents, nitric oxide, radioactively tagged particles and/or a variety of other gaseous agents.

The respiratory circuit 12 generally includes a standard respiratory circuit "Y" 16, a filter/recycler unit 18, and a respirator/gas supply unit 20. The Y 16, which may be interfaced with the patient 14 via a mouth piece or intratracheal tube, includes appropriate one-way valves for allowing one-way flow of gases from the respirator/gas supply unit 20 to the patient 14, and one-way gas flow from the patient 14 into an expiration line 22 that extends to the filter/recycler unit 18. It will be appreciated that the expired gas stream will include a combination of respiratory gases and anesthetic/therapeutic gases. This expired stream may include a number of potentially harmful materials and is therefore handled carefully. In this regard, the filter/recycler unit 18 removes harmful materials from the expired gas stream. The remaining components of the gas stream, such as anesthetic agents and certain respiratory components are recovered for reuse. The recovered components are delivered to the respiratory/gas supply unit 20. The respiratory/gas supply unit, supplies the desired mixture of respiratory and anesthetic/therapeutic components to the patient 14. In this regard, the respiratory/gas supply unit 20 includes a supply, e.g., gas canisters, of the required gases. These gases are used in combination with the recovered components from the filter/recycler unit 18 to provide the desired gas mixture to the patient 14.

As will be readily appreciated, it is important to monitor the respiratory circuit during a medical procedure in order to insure that the patient 14 is receiving the desired mixture of gases. Such monitoring is conducted in accordance with the present invention by using the analyzer 10. Generally, the analyzer 10 includes an illumination source 24, optics 26, a modulator unit 28, a beam splitter 30 for separating a modulated signal into sample and reference signals, a transmitter/detector unit 32, a processing unit 34, and a display 36. Each of these components is described in turn below.

The source 24 provides illumination having multiple wavelengths. Preferably, the source 24 transmits infrared illumination having a spectral composition sufficient for analyzing multiple respiratory and anesthetic components of the sample gas, i.e., the respiratory stream. In this regard, various components of the sample gas have identifiable spectral absorption characteristics within the 2–12 micron wavelength range. The illustrated source 24 comprises a broad band, black body source for providing a high intensity of illumination across the 2–12 micron wavelength range. A suitable source is described in detail in U.S. patent application Ser. No. 08/605,973 entitled "Optical System With An Extended, Imaged Source" filed Feb. 23, 1996, which is incorporated by reference herein in its entirety. As described in that application, the source 24 is preferably operated at a temperature greater than 900° C. to provide the desired illumination.

The illumination from the source 24 is transmitted to the modulator 28 via the optics 26. The illumination entering modulator 28 is preferably somewhat collimated, i.e., its divergence is limited. In this regard, the optics may include a collimator for transmitting a narrow beam of illumination, lenses for focusing the illumination and/or mirrors for defining a folded optical path so as to increase the optical path length, for a given physical separation, between the source 24 and modulator 28.

Figure 2:
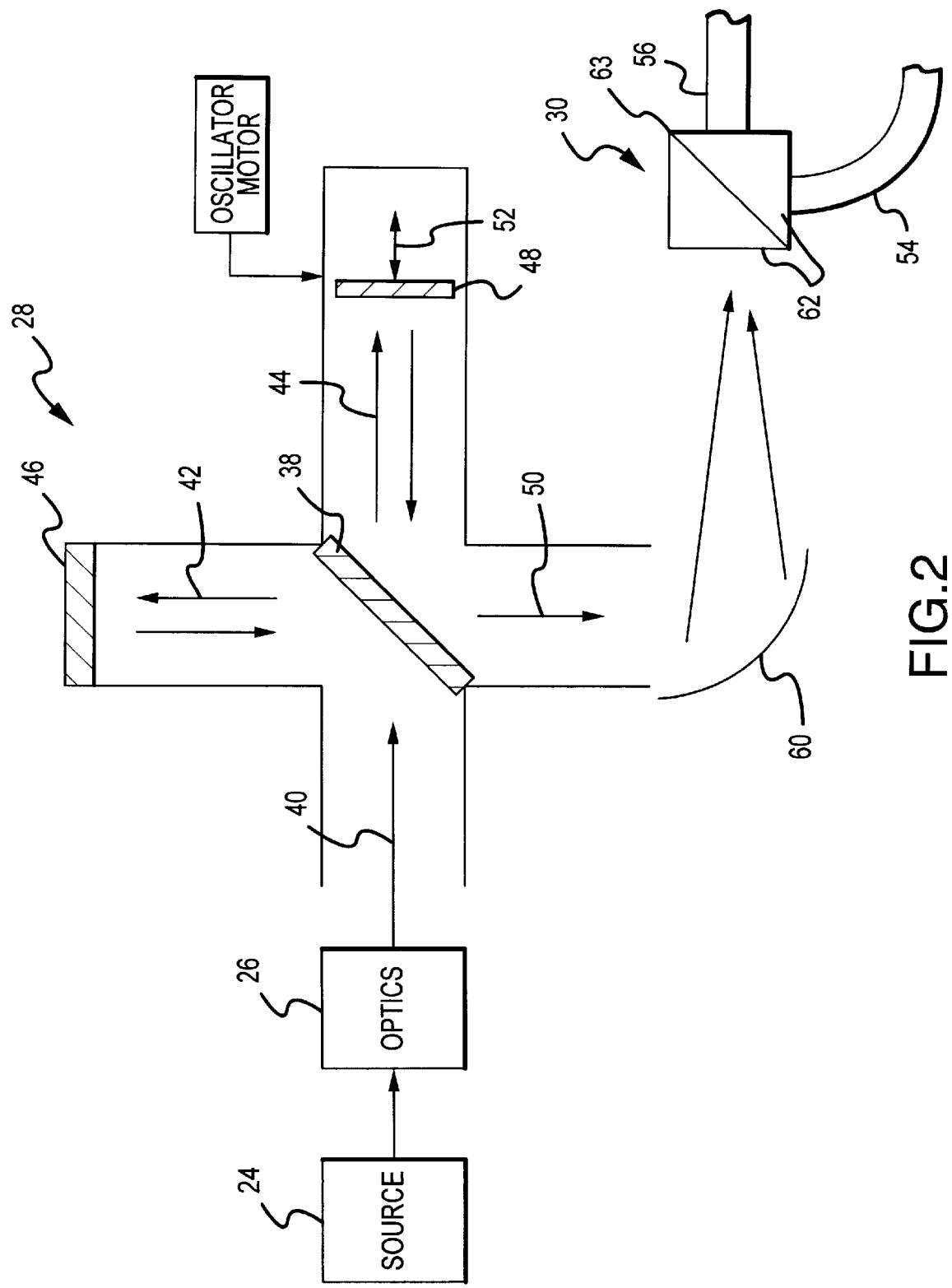
FIG. 2 illustrates a signal modulator of the analyzer of FIG. 1.

The modulator 28 is operative for modulating different wavelength components of the transmitted illumination at different modulating frequencies. The illustrated modulator 28, as best shown in FIG. 2, includes a Michelson interferometer for outputting a modulated signal that is the Fourier transform of the received illumination. In this regard, the modulator 28 includes a beam splitter 38, such as a partially aluminized mirror, for dividing the input illumination 40 into two substantially equal portions transmitted on separate pathways as generally indicated by arrows 42 and 44. The illumination portion 42 transmitted along first pathway reflects off of stationary mirror 46 and returns to beam splitter 38. Illumination 44 transmitted along the second pathway reflects off of moveable mirror 48 and is reflected back to beam splitter 38. Portions of the illumination reflected by stationary mirror 46 and moveable mirror 48 are recombined at the beam splitter 38 to form modulated signal 50. Remaining portions of the illumination reflected by mirrors 46 and 48 are transmitted back towards optics 26, defining a signal that complements modulated signal 50. This complementary signal may be used as a reference signal thereby eliminating the illustrated beam splitter 30.

The desired Fourier transform is achieved by moving movable mirror 48. In this regard, oscillator motor 52 is used to drive the movable mirror 48 in a linear reciprocating manner as generally indicated by arrows 52. In this manner, the path length traveled by illumination on path 42 and, hence, the phase difference between the illumination portions transmitted along paths 42 and 44, vary as a function of time. In this regard, the motion of moveable mirror 48 can be controlled, in a manner that is well-known, such that the modulated signal is the Fourier transform of the received illumination.

The use of the modulated signal 50 has certain advantages for in-stream, multiple component infrared analysis as will be discussed in more detail below. The modulated signal 50 is also well suited for focusing onto the end of a fiber optic light guide. In particular, the modulated signal 50 exiting modulator 28 is well-collimated as a result of processing by optics 26 and modulator 28. In this regard, the illustrated analyzer 10 employs fiber optics 54 and 56 to convey the modulated signal 50 from the modulator 28 to an analysis location 58 (FIG. 1) in the respiratory circuit 12 proximate to the patient 14. Such fiber optics 56 and 58 allow for separation of the source 24, optics 26, and modulator 28 from the transmitter/detector unit 32 so as to avoid unnecessary cluttering of the working space near the patient 14, without unduly affecting optical efficiency. The fiber optics 56 and 58 employed in this regard are preferably suitable for transmitting infrared illumination. Suitable chalcogenide glass fiber optics are manufactured by Amorphous Materials, Inc. of Garland, Tex. The illustrated fiber optics 56 and 58 include a sample light guide 56 and a reference light guide 58 as will be understood from the description below.

The illustrated analyzer 10 employs a concave mirror 60 and a beam splitter cube 63 to couple the modulated signal 50 output by the modulator 28 to the sample 58 and reference 58 light guides. In this regard, the beam splitter cube 63 is formed from two prismatic blocks 64 and 66. An appropriate silver or other coating 64 is provided at one or both of the block interface surfaces such that half of the received signal is transmitted to light guide 54 and the remaining signal portion is transmitted to light guide 56. The ends the light guides 54 and 56 are located approximately in a focal plane of the concave mirror such that the modulated signal 50 is efficiently transmitted into the light guides 54 and 56. Alternatively, a complementary signal transmitted from the modulator 28 towards optics 26, as discussed a above, may be coupled to the reference light guide 38. As a further alternative, the reference signal and corresponding optical path may be eliminated and stored reference signal information may be used for processing.

The sample 54 and reference 56 light guides are used to transmit corresponding sample and reference signals to the transmitter/detector unit 32. The transmitter/detector unit preferably supports the sample 54 and reference 56 light guides, and a detector system, such that the sample signal is transmitted through a portion of the patient respiratory circuit 12 to the detector system and the reference signal is transmitted to the detector system without traversing the patient respiratory circuit 12. The received sample and reference signals can then be processed, as described below, to provide composition information regarding the patient's respiratory stream.

Figure 3:
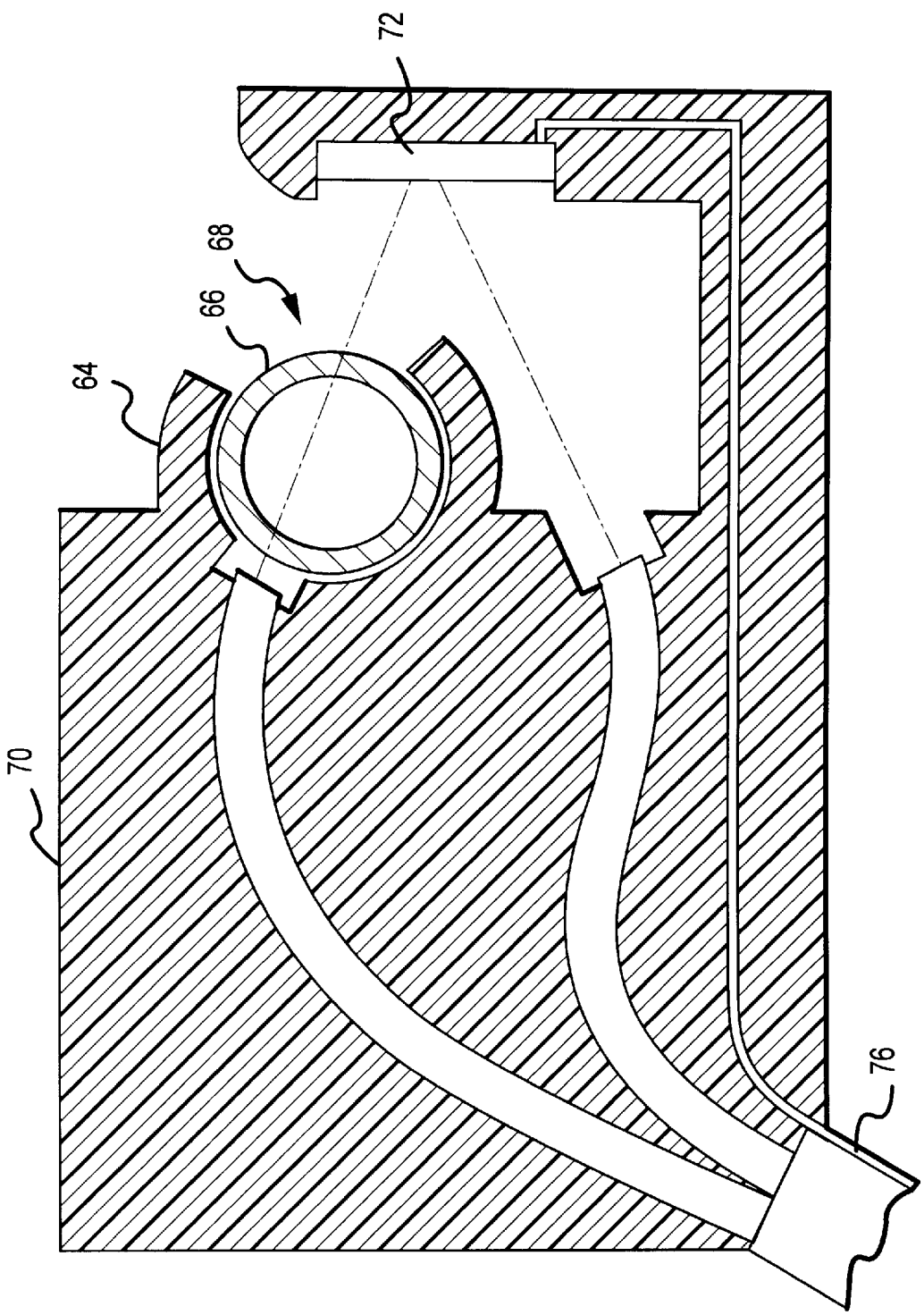
FIG. 3 illustrates an embodiment of a transmitter/detector unit according to the present invention.

One embodiment of the transmitter/detector unit 32 is shown in FIG. 3. The illustrated unit 32 includes a mount 64 for engaging a respiratory circuit conduit 66. Any suitable mechanism for engaging the conduit 66 may be used in this regard including for example, various clamps and fasteners. The illustrated mount 64 is a molded plastic channel dimensioned to receive the conduit 66 through an open end 68 thereof and to securely retain the conduit 66 therein. Within the unit housing 70, which may be formed from plastic or other suitable material, the sample light guide 54 is mounted such that its end is aligned to direct the sample signal through the conduit 66 to impinge on a detector surface of a detector system 72. It will be appreciated that the conduit 66 is at least partially formed from materials suitable for transmitting infrared signals. The reference light guide 56 is supported within housing 70 such that its end is aligned to transmit the reference signal to the detector system 72 without traversing the conduit 66. Preferably, the path lengths defined by the sample and reference signals are substantially equal in length. The sample and reference signals are received by separate portions of the detector system 72, or are alternately transmitted to the system 72 by operation of an optical chopper or the like (not shown) for separate processing. In this regard, the detector system 72 or its separate portions are read out on a periodic basis, for example, 20 times per second, to achieve the desired sampling rate. The output signals 74 (FIG. 1) read out from the detector system 72 are transmitted to a remotely located processing unit 34 via electrical lead 76.

Figure 4:
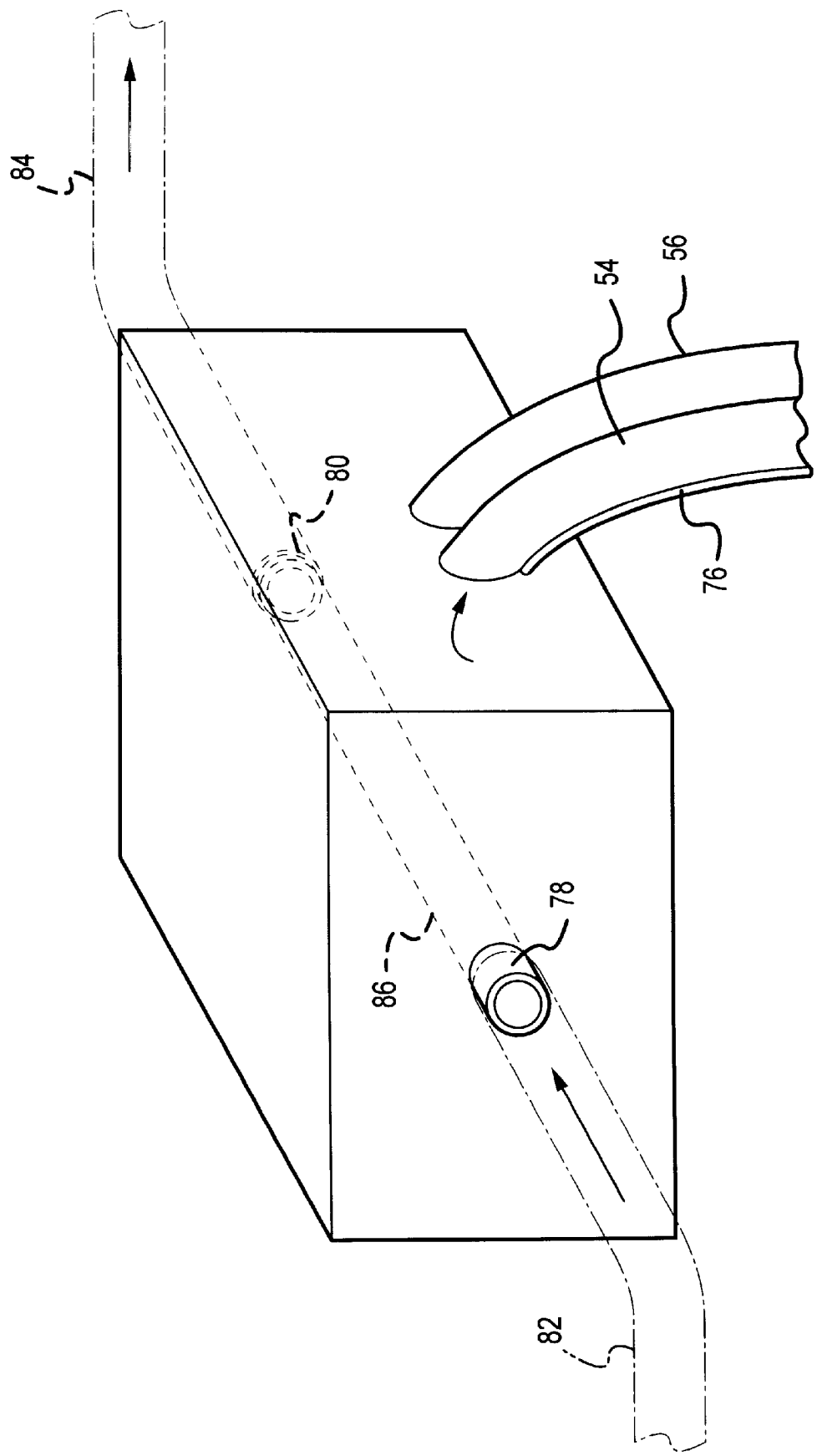
FIG. 4 illustrates an alternative transmitter/detector unit in accordance with the present invention.

FIG. 4 generally illustrates an alternative implementation of the transmitter/detector unit 32. Rather than engaging a separate respiratory circuit conduit, the unit 32' of FIG. 4 is interposed within the respiratory circuit 12. The unit 32' includes an entrance adapter mount 78 and an exit adapter mount 80. The entrance adapter 78 sealingly engages a first section 82 of the respiratory circuit 12 and the exit adapter 80 sealingly engages a second section 84 of the circuit 12. An internal gas pathway 86 between the adapters 78 and 80 is integrally formed within the unit 32'. The unit 32' further includes ports 88 for receiving the sample light guide 54, reference light guide 56 and electrical lead 76.

Figure 5:
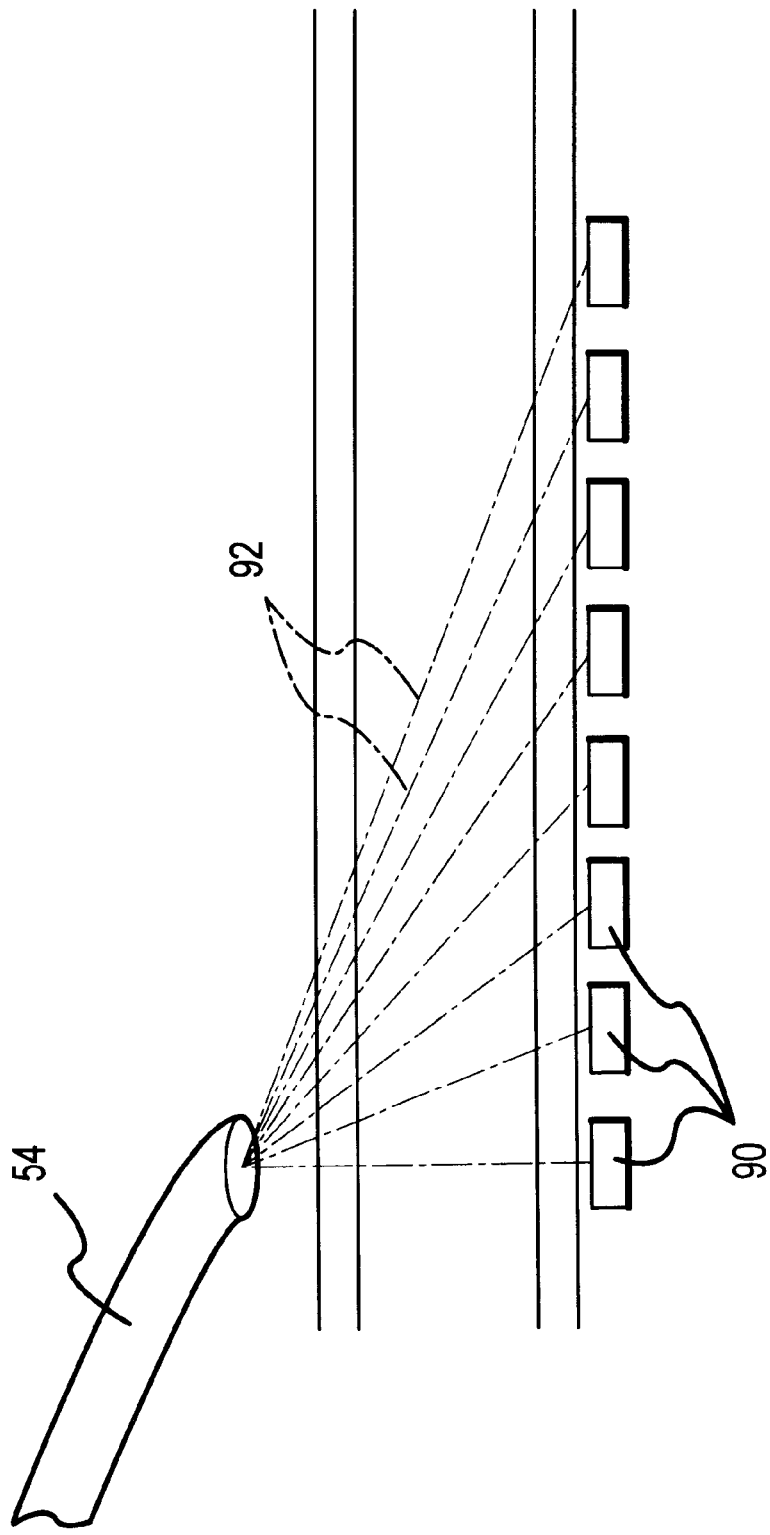
FIG. 5 illustrates an alternative embodiment of the transmitter/detector unit including multiple detectors.

FIG. 5 generally shows an alternative sample light guide/detector system configuration. In the illustrated configuration, the detector system 72' includes a number of detectors 90. For example, the number of detectors 90 may be equal to or greater than the number of components to be monitored by the analyzer 10. The detectors 90 are arranged so as to define different optical pathways 92 with different path lengths between the sample light guide 54 and the respective detectors 90. These multiple path lengths will allow the analyzer 10 to monitor multiple components having different absorption sensitivities with similar measurement accuracy.

Referring again the FIG. 1, the output from the transmitter/detector unit 32, generally indicated by arrow 74, is transmitted to a processing unit 34 that includes deconvolution electronics 94 and processor 96. The output signals 74 corresponding to the sample signal and reference signal are deconvolved by the processing electronics 94, in a manner that is well-known, to provide deconvolved signals that generally correspond to the absorption spectra of the sample and reference signals. These deconvolved signals are analyzed by processor 96 using standard chemometric calculations to identify and quantify the components of interest in the gas sample. The resulting composition information is then transmitted to display 36 for real time monitoring by a technician or other analyzer user.

Figure 6:
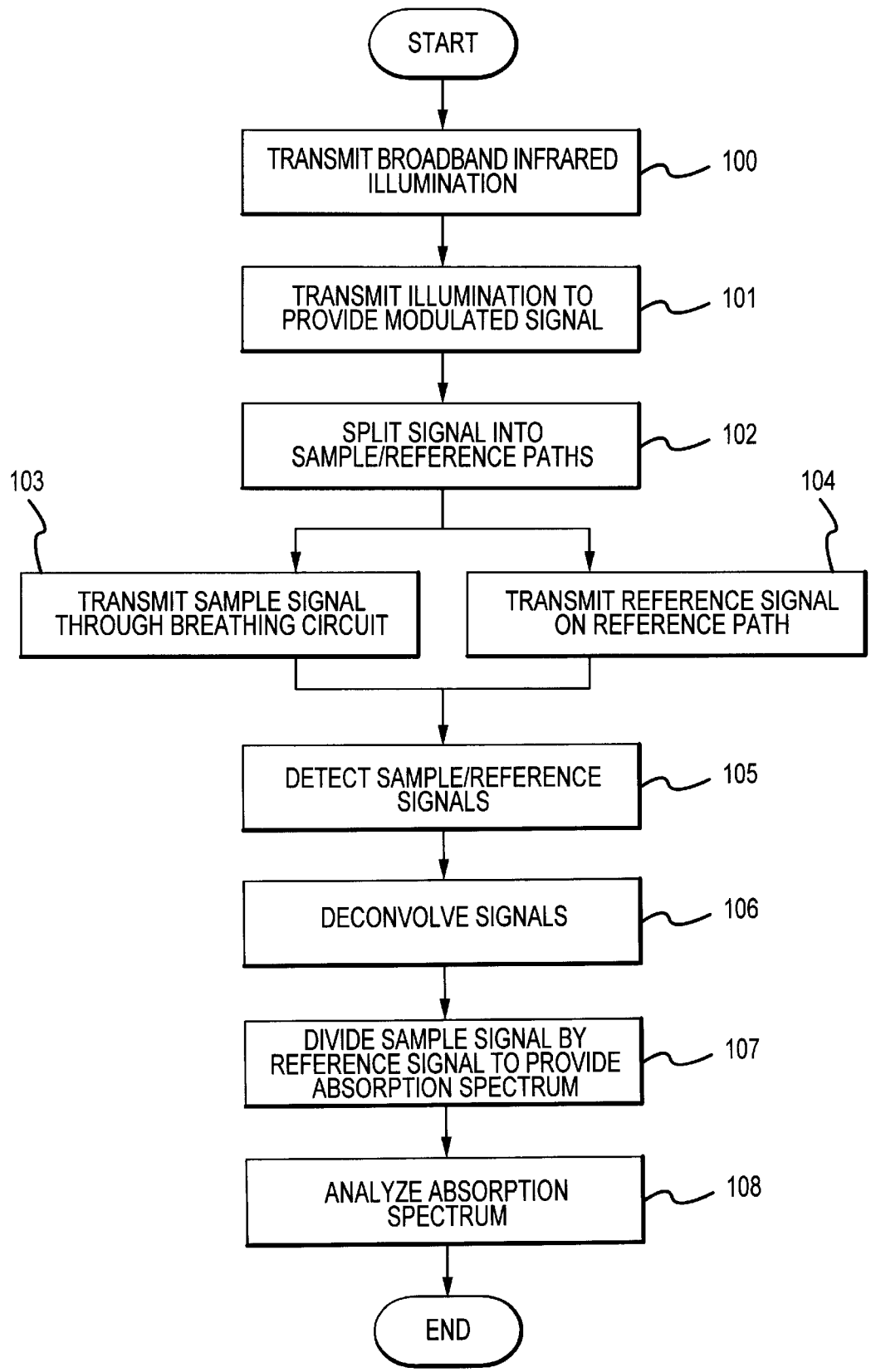
FIG. 6 is a flowchart illustrating analyzer methodology in accordance with the present invention.

The corresponding methodology of the present invention is generally illustrated in FIG. 6. The process is initialed, in a preferred implementation, by transmitting (100) broad band infrared illumination. The transmitted illumination is transformed (101), by a Michelson interferometer or other modulator, to provide a modulated signal. The modulated signal is split (102) into sample and reference pathways and transmitted (103 and 104) to the transmitter/analyzer unit by corresponding sample and reference light guides. In particular, the sample signal is transmitted (103) to the detector system via the respiratory circuit and the reference signal is transmitted (104) the detector system without traversing the respiratory circuit.

The detector system detects (105) the sample and reference signals and provides output signals corresponding thereto. The output signals are transmitted to a processing system where the signals are deconvolved (106), and the sample signal is then divided (107) by the reference signal using processor to provide absorption spectra indicative of the sample gas composition. In this regard, it is known that absorption is proportional to the logarithm of the quotient of the sample modified intensity divided by the reference intensity. The resulting absorption spectra are then analyzed (108) using standard chemometric calculations in order to yield composition information which can be displayed to the user.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed is:

1. An apparatus for use in monitoring a respiratory stream of a patient, comprising:

a source means for transmitting illumination including a first wavelength portion and a second wavelength portion;

modulating means for modulating said first wavelength portion at a first modulating frequency and said second wavelength portion at a second modulating frequency different than said first modulating frequency to provide a modulated signal including said modulated wavelength portions;

transmission means for transmitting said modulating signal through said respiratory stream of said patient; and analyzer means for analyzing said transmitted modulated signal so as to obtain composition information regarding said respiratory stream of said patient.

2. An apparatus as set forth in claim 1, wherein said transmission means transmits said modulated signal through a portion of a patient respiratory circuit.

3. An apparatus as set forth in claim 1, wherein said source means comprises an infrared illumination source.

4. An apparatus as set forth in claim 1, wherein said modulating means comprises means for receiving illumination from said source and providing an output signal that is a Fourier transform of the received illumination.

5. An apparatus as set forth in claim 1, wherein said modulating means comprises an interferometer for receiving illumination from said source, separating said received illumination into two illumination portions, transmitting said separated illumination portions on two separate paths, at least one of said paths having a variable path length, and recombining said illumination portions to form said modulated signal.

6. An apparatus as set forth in claim 1, wherein said transmission means comprises fiber optic means for transmitting said modulated signal between said source means and said analyzer means.

7. An apparatus as set forth in claim 6, wherein said fiber optic means is disposed between said modulating means and said respiratory stream.

8. An apparatus as set forth in claim 1, wherein said analyzer means comprises multiple illumination detectors for receiving illumination transmitted through said respiratory stream on multiple paths having different path lengths.

9. An apparatus as set forth in claim 1, wherein said transmission means comprises a probe for interconnection to a patient respiratory circuit so as to facilitate transmission of said modulated signal through said respiratory stream.

10. An apparatus as set forth in claim 9, wherein said probe supports a detector for detecting illumination transmitted through said respiratory stream.

11. An apparatus for use in monitoring a respiratory stream of a patient comprising:

source means for transmitting illumination including a first wavelength portion and a second wavelength portion;

Fourier transform means for receiving said illumination from said source means and providing an output signal that is a Fourier transform of the received illumination;

transmission means for transmitting said transformed signal through said respiratory stream of said patient; and analyzer means for analyzing said transmitted transformed signals so as to obtain composition information regarding said respiratory stream of said patient.

12. An apparatus as set forth in claim 11, wherein said transmission means transmits said modulated signal through a portion of a patient respiratory circuit.

13. An apparatus as set forth in claim 11, wherein said Fourier transform means comprises an interferometer for receiving illumination from said source, separating said received illumination into two illumination portions, transmitting said separated illumination portions on two separate paths, at least one of said paths having a variable path length, and recombining said illumination portions to form said modulated signal.

14. An apparatus as set forth in claim 11, wherein said transmission means comprises fiber optic means for transmitting said modulated signal between said source means and said analyzer means.

15. An apparatus as set forth in claim 11, wherein said analyzer means comprises multiple illumination detectors for receiving illumination transmitted through said respiratory stream on multiple paths having different path lengths.

16. An apparatus as set forth in claim 11, wherein said transmission means comprises a probe for interconnection to a patient respiratory circuit so as to facilitate transmission of said modulated signal through said respiratory stream.

17. An apparatus for monitoring a respiratory stream of a patient comprising:

a) a transmitter/detector unit disposed on a respiratory circuit of said respiratory stream including 1) mounting means for engaging a portion of said respiratory circuit;

2) first support means for supporting fiber optics for transmitting an infrared, frequency modulated signal through said engaged portion of said respiratory circuit; and 3) second support means for supporting a detector system for detecting the infrared, frequency modulated signal transmitted through the engaged portion of the respiratory circuit and providing an output signal based on the detected, modulated signal;

wherein the fiber optics and detector system are supported in optical alignment with the engaged portion of the respiratory circuit disposed therebetween;

b) optical means for optically interconnecting said transmitter/detector unit to a remotely located illumination source; and c) electrical means for electrically interconnecting said transmitter/detector unit to a remotely located processor for analyzing said output signal.

18. An apparatus as set forth in claim 17, wherein said detector system comprises a plurality of detectors.

19. An apparatus as set forth in claim 17, wherein said mounting means comprises first and second adaptors for engaging first and second conduit sections of said respiratory circuit such that said transmitter detector unit is interposed within said circuit.

20. An apparatus as set forth in claim 17, wherein said transmitter/detector unit further comprises means for supporting second fiber optics for transmitting a reference signal to the detector system.

21. A method for use in monitoring a respiratory stream of a patient, comprising the steps of:

operating a source to provide infrared illumination;

modulating the infrared illumination on a wavelength dependent basis to provide a modulated signal wherein a first wavelength is modulated at a first modulating frequency and a second wavelength is modulated at a second modulating frequency;

transmitting said modulated signal through the respiratory stream;

detecting said modulated signal transmitted through the respiratory stream; and analyzing said detected signal to determine composition information regarding said stream.

22. A method as set forth in claim 21, wherein said step of modulating comprises operating a Michelson interferometer to transform said illumination into said modulated signal.

23. A method as set forth in claim 21, wherein said step of transmitting comprises using fiber optics to convey said modulated signal.

24. A method as set forth in claim 21, wherein said step of transmitting comprises irradiating said respiratory stream in a patient respiratory circuit.

25. A method as set forth in claim 21, wherein said step of analyzing comprises comparing said detected signal to a reference signal.

* * * * *